United States Patent
Kulber

(10) Patent No.: US 10,905,558 B2
(45) Date of Patent: Feb. 2, 2021

(54) MENISCUS FOR JOINT RECONSTRUCTION

(71) Applicant: Cedars-Sinai Medical Center, Los Angeles, CA (US)

(72) Inventor: David A. Kulber, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 138 days.

(21) Appl. No.: 15/876,609

(22) Filed: Jan. 22, 2018

(65) Prior Publication Data

US 2018/0140425 A1    May 24, 2018

Related U.S. Application Data

(62) Division of application No. 14/946,089, filed on Nov. 19, 2015, now abandoned.

(60) Provisional application No. 62/082,033, filed on Nov. 19, 2014.

(51) Int. Cl.
*A61F 2/30* (2006.01)

(52) U.S. Cl.
CPC ............ *A61F 2/30756* (2013.01); *A61F 2002/30757* (2013.01); *A61F 2002/30764* (2013.01)

(58) Field of Classification Search
CPC ............ A61F 2/30756; A61F 2/3872; A61F 2002/30757; A61F 2002/30764; A61F 2002/30759
See application file for complete search history.

(56) References Cited

U.S. PATENT DOCUMENTS

| 6,017,366 | A | 1/2000 | Berman |
| 8,834,568 | B2 | 9/2014 | Shapiro |
| 2011/0190887 | A1* | 8/2011 | Shapiro .................... A61F 2/08 623/14.12 |

FOREIGN PATENT DOCUMENTS

WO    2013086404 A1    6/2013

OTHER PUBLICATIONS

Delacruz et al. First Metatarsophalangeal Joint Interpositional Arthroplasty Using a Meniscus Allograft for the Treatment of Advanced Hallux Rigidus:Surgical technique and Short-term Results. Foot & Ankle Specialist (2011). 4(3):157-164.
Kulber, D.A. Surgeon Employs Novel Technique Using Cadaver Meniscus to Reconstruct Finger Joints. Cedars-Sinai Medical Center Press Release (2014); 2 pages.
Ochi et al, Allogeneic Deep Frozen Meniscal Graft for Repair of Osteochondral Defects in the Knee Joint, 1995, Arch. Orthop. Trauma Surg., vol. 114, pp. 260-266.
Yao et al. Preserving the Posttrapeziectomy Space with a Human Acellular Dermal Matrix Spacer: A Pilot Case Series of Patients with Thumb Carpometacarpal Joint Arthritis. Plast Reconstr Surg Glob Open (2013). 1(7):7 pages.

\* cited by examiner

*Primary Examiner* — Dinah Baria
(74) *Attorney, Agent, or Firm* — Linda B. Huber; Nixon Peabody LLP

(57) ABSTRACT

The invention provides treatment methods of using meniscus to repair injured and/or arthritic joints, for example, small hand joints including but not limited to radiocarpal, metacarpophalangeal, and interphalangeal joints. The invention also provides various implants made of meniscus for injured and/or arthritic joints.

13 Claims, 7 Drawing Sheets

MENISCUS FOR JOINT RECONSTRUCTION

CROSS-REFERENCE TO RELATED APPLICATIONS

This application is a divisional of U.S. patent application Ser. No. 14/946,089 filed Nov. 19, 2015, which also includes a claim of priority under 35 U.S.C. § 119(e) to U.S. provisional patent application No. 62/082,033, filed on Nov. 19, 2014, the contents of which are herein incorporated by reference in its entirety as though fully set forth.

FIELD OF THE INVENTION

The invention relates to methods and implants for reconstructing joints.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The most common cause of disability among US adults is damaged or arthritic small joints in the hand. Patients feel severe pain and have limited hand function. The joints may be reconstructed with synthetic joint implants, for example, those made of hard silicone and pyrolytic carbon. However, synthetic joint implants are subject to infection, and may loosen or break over time, leaving patients with lasting pain or in need of follow-up surgeries.

To solve these problems, this invention provides methods of using meniscus to reconstruct joints, as well as products made of meniscus for this procedure.

SUMMARY OF THE INVENTION

Various embodiments of the present invention provide an implant for implantation into a subject's joint or for cartilage repair of an osteochondral defect or damage. In various embodiments, the implant may comprise or may consist essentially of or may consist of: a piece of tissue harvested from a meniscus, wherein the piece of tissue is dimensioned to cover a surface of a bone in the joint, or dimensioned to replace a defective or damaged portion of the cartilage of the osteochondral defect or damage. In some embodiments, the implant is for implantation into a subject's joint. In some embodiments, the implant is for cartilage repair of the osteochondral defect or damage. In various embodiments, the subject's joint is a small, medium, or large joint.

Various embodiments of the present invention provide a method of manufacturing an implant for implantation into a subject's joint, or for repairing cartilage due to a osteochondral defect or damage. In various embodiments, the method may comprise or may consist essentially of or may consist of: obtaining a piece of tissue from a meniscus; and dimensioning the piece of tissue for covering a surface of a bone in the joint, or dimensioning the piece of tissue for replacing the defective or damaged portion of the cartilage of the osteochondral defect or damage, whereby the dimensioned piece of tissue is the manufactured implant.

Various embodiments of the present invention provide a method of treating a subject's joint. In various embodiments, the method may comprise or may consist essentially of or may consist of: providing a piece of tissue harvested from a meniscus, wherein the piece of tissue is dimensioned to cover a surface of a bone in the joint; exposing the joint; preparing (e.g., burring or debriding) the surface; inserting the piece of tissue into the joint; securing the piece of tissue to the surface; and closing the joint. In various embodiments, before closing the joint, the method further comprises: providing a second piece of tissue harvested from a meniscus, wherein the second piece of tissue is dimensioned to cover a second surface of a second bone in the joint; preparing the second surface; inserting the second piece of tissue into the joint; and securing the second piece of tissue to the second surface.

Various embodiments of the present invention provide a method of cartilage repair of an osteochondral defect or damage. In various embodiments, the method may comprise or may consist essentially of or may consist of: providing a piece of tissue harvested from a meniscus, wherein the piece of tissue is dimensioned replace the defective or damaged portion of the cartilage of the osteochondral defect or damage; removing the defective or damaged portion of the cartilage; inserting the piece of tissue into the removed portion of the cartilage; and securing the piece of tissue to the cartilage.

Various embodiments of the present invention provide a kit for treating a subject. In various embodiments, the kit may comprise or may consist essentially of or may consist of: comprising: an implant as disclosed herein; and instructions for using the implant to treat the subject. In various embodiments, the kit further comprises one or more securements for securing the implant into the subject's joint. In accordance with the present invention, the securement can be a suture, anchor, suture anchor, fibrin glue, screw, bolt, nail, pin, staple, fastener, ligament, or adhesive, or a combination thereof.

Various implants, methods and kits of the present invention find utility in the treatment of various medical conditions of joints, for example, small joints like finger and hand joints, medium joints like wrist joints, and large joints like shoulder joints.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 6A-6E are photographs, FIGS. 6F-6G are X-ray images, and FIGS. 6H-6L are renderings. The radiolunate facet and proximal capitate articular surfaces are debrided, and a meniscus 606 was outlined (3 cm×1 cm) for covering the articular surfaces and then cut accordingly (6A and 6H); osteochondral defects were inset with the meniscus 606 (6B and 6I); the meniscus 606 was sutured to the articular surfaces (6C and 6J); the meniscus 606 and the articular surfaces were coated with fibrin sealant glue (6D and 6K); and the joint was closed while joint space was preserved intraoperatively (6E and 6L).

DETAILED DESCRIPTION OF THE INVENTION

Figure 1:
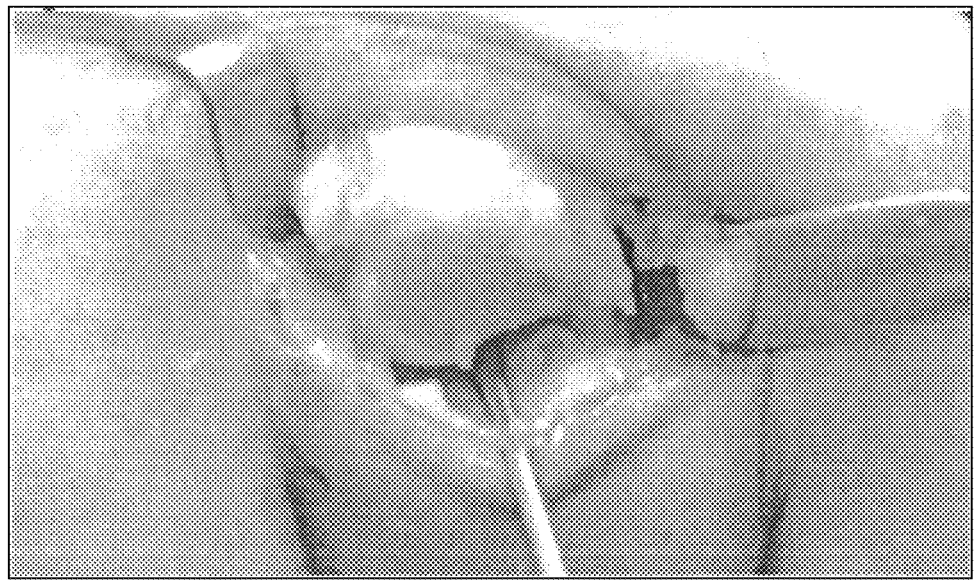
FIG. 1 depicts, in accordance with various embodiments of the invention, the small joint reconstruction on Patient 1.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); and Singleton and Sainsbury, Dictionary of Microbiology and Molecular Biology 3$^{rd}$ ed., revised ed., J. Wiley & Sons (New York, N.Y. 2006); provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and increasing a subject's quality of life. As non-limiting examples, "beneficial results" or "desired results" may be alleviation of one or more symptom(s), diminishment of extent of the deficit, stabilized (i.e., not worsening) state of a joint condition, delay or slowing of a joint condition, and amelioration or palliation of symptoms associated with a joint condition.

"Diseases", "conditions" and "disease conditions," as used herein may include, but are in no way limited to any form of joint-related condition, disease or disorder, for example, damaged joints and arthritic joints.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., a damaged or arthritic joint) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

To avoid the issues of synthetic joint implants, the inventor uses a biological material, cadaver meniscus (e.g., from the knee), for joint reconstruction. Cadaver meniscus is a resilient and spongy cushion that can prevent joint bones from rubbing against each other. Briefly, as one non-liming example, the reconstruction procedure when applied to a joint in the finger has the following steps: (1) opening an affected finger joint (e.g., metacarpophalangeal and interphalangeal joints); (2) preparing an articular surface of the finger joint (for example, removing remaining or damaged cartilage, decorticating the bone to expose the medullary cortex, and using reamers to create cup and/or cup joint configurations); (3) inserting and suturing one or more pieces (e.g., 1, 2, 3, 4, 5) of pre-tested cadaver meniscus onto the prepared articular surface; and (4) closing the reconstructed finger joint. Optionally, fibrin glue can be used to coat the meniscus piece(s) and articular surface. The implanted cadaver meniscus fits neatly into the finger joint, is revascularized, and gets incorporated into the finger joint as blood flows through. All patients who have undergone this procedure have improvements in pain levels and motion ranges of the affected joints.

Implants

In various embodiments, the present invention provides an implant for implantation into a subject's joint. In some embodiments, the implant comprises a piece of tissue harvested from a meniscus, and the piece of tissue is dimensioned to cover a surface of a bone in the joint. In other embodiments, the implant may consist of or consist essentially of a piece of tissue harvested from a meniscus, and the piece of tissue is dimensioned to cover a surface of a bone in the joint. In various embodiments, the surface is an articular surface.

In some embodiments, the implant comprises a piece of tissue harvested from a meniscus, and the piece of tissue is dimensioned to repair an osteochondral damage or defect. For example, when a portion of a subject's cartilage is removed due to the osteochondral damage or defect, the implant can be used to replace portion of the removed cartilage.

In various embodiments, the piece of tissue is shaped to be round or generally round, oval or generally oval, square or generally square, or rectangular or generally rectangular. In certain embodiments, the piece of tissue is shaped to be flat, saucer-shaped or cup-shaped.

In various embodiments, the piece of tissue is dimensioned to be about 0.2-4.0 $cm^2$. In various embodiments, the piece of tissue is dimensioned to be about 0.2-0.3, 0.3-0.4, 0.4-0.5, 0.5-0.6, 0.6-0.7, 0.7-0.8, 0.8-0.9, 0.9-1, 1-2, 2-3, or 3-4 $cm^2$. In certain embodiments, the piece of tissue is dimensioned to be about 0.2, 0.3, 0.4, 0.5, 0.6, 0.7, 0.8, 0.9, 1, 2, 3, or 4 $cm^2$. In particular embodiments, the piece of tissue is dimensioned to be about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 $cm^2$.

In various embodiments, the piece of tissue has a dimension (e.g., diameter, diagonal, width, or length) of about 0.2-4.0 cm. In various embodiments, the piece of tissue has a dimension (e.g., diameter, diagonal, width, or length) of about 0.2-0.3, 0.3-0.4, 0.4-0.5, 0.5-0.6, 0.6-0.7, 0.7-0.8, 0.8-0.9, 0.9-1, 1-2, 2-3, or 3-4 cm. In certain embodiments, the piece of tissue has a dimension (e.g., diameter, diagonal, width, or length) of about 0.3-0.5 or 0.5-3 cm. In certain embodiments, the piece of tissue has a dimension (e.g., diameter, diagonal, width, or length) of about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 cm. In some embodiments, the piece of tissue has dimensions of about 0.5 cm×0.5 cm, 0.5 cm×1 cm, 0.5 cm×2 cm, 0.5 cm×3 cm, 0.5 cm×4 cm, 1 cm×1 cm, 1 cm×2 cm, 1 cm×3 cm, 1 cm×4 cm, 2 cm×2 cm, 2 cm×3 cm, 2 cm×4 cm, 3 cm×3 cm, 3 cm×4 cm, or 4 cm×4 cm.

In various embodiments, the piece of tissue has a thickness of about 0.1-1.0 cm. In various embodiments, the piece of tissue has a thickness of about 0.1-0.2, 0.2-0.3, 0.3-0.4, 0.4-0.5, 0.5-0.6, 0.6-0.7, 0.7-0.8, 0.8-0.9, or 0.9-1 cm. In certain embodiments, the piece of tissue has a thickness of about 0.1-0.2 or 0.2-1 cm. In certain embodiments, the piece of tissue has a thickness of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm. The thickness can be uniform or non-uniform. For example, for a saucer-shaped tissue, the center of the tissue can be thicker than the edges.

In various embodiments, the second piece of tissue is shaped to be round or generally round, oval or generally oval, square or generally square, or rectangular or generally rectangular. In certain embodiments, the second piece of tissue is shaped to be flat, saucer-shaped or cup-shaped.

In various embodiments, the second piece of tissue is dimensioned to be about 0.2-4.0 cm$^2$. In various embodiments, the second piece of tissue is dimensioned to be about 0.2-0.3, 0.3-0.4, 0.4-0.5, 0.5-0.6, 0.6-0.7, 0.7-0.8, 0.8-0.9, 0.9-1, 1-2, 2-3, or 3-4 cm$^2$. In certain embodiments, the second piece of tissue is dimensioned to be about 0.2, 0.3, 0.4, 0.5, 0.6, 0.7, 0.8, 0.9, 1, 2, 3, or 4 cm$^2$. In particular embodiments, the second piece of tissue is dimensioned to be about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm$^2$.

In various embodiments, the second piece of tissue has a dimension (e.g., diameter, diagonal, width, or length) of about 0.2-4.0 cm. In various embodiments, the second piece of tissue has a dimension (e.g., diameter, diagonal, width, or length) of about 0.2-0.3, 0.3-0.4, 0.4-0.5, 0.5-0.6, 0.6-0.7, 0.7-0.8, 0.8-0.9, 0.9-1, 1-2, 2-3, or 3-4 cm. In certain embodiments, the second piece of tissue has a dimension (e.g., diameter, diagonal, width, or length) of about 0.3-0.5 or 0.5-3 cm. In certain embodiments, the second piece of tissue has a dimension (e.g., diameter, diagonal, width, or length) of about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 cm. In some embodiments, the second piece of tissue has dimensions of about 0.5 cm×0.5 cm, 0.5 cm×1 cm, 0.5 cm×2 cm, 0.5 cm×3 cm, 0.5 cm×4 cm, 1 cm×1 cm, 1 cm×2 cm, 1 cm×3 cm, 1 cm×4 cm, 2 cm×2 cm, 2 cm×3 cm, 2 cm×4 cm, 3 cm×3 cm, 3 cm×4 cm, or 4 cm×4 cm.

In various embodiments, the second piece of tissue has a thickness of about 0.1-1.0 cm. In various embodiments, the second piece of tissue has a thickness of about 0.1-0.2, 0.2-0.3, 0.3-0.4, 0.4-0.5, 0.5-0.6, 0.6-0.7, 0.7-0.8, 0.8-0.9, or 0.9-1 cm. In certain embodiments, the second piece of tissue has a thickness of about 0.1-0.2 or 0.2-1 cm. In certain embodiments, the second piece of tissue has a thickness of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm. The thickness can be uniform or non-uniform. For example, for a saucer-shaped tissue, the center of the tissue can be thicker than the edges.

As used herein, "round" describes a shape that is round or generally round. As used herein, "oval" describes a shape that is oval or generally oval. As used herein, "square" describes a shape that is square or generally square. As used herein, "rectangular" describes a shape that is rectangular or generally rectangular. "Generally round, oval, square, or rectangular" as used herein means that one of ordinary skill in the art would have recognized that an object resembles a round oval, square or rectangular shape, while the object may not be perfectly round, oval, square or rectangular. For example, a cadaveric meniscus as a raw material may need to be trimmed to produce the various implants as described in the present invention. In some cases, the cadaveric meniscus may be trimmed with a machine to produce perfectly round, oval, square or rectangular implants. In other cases, however, the cadaveric meniscus may be trimmed by hand to produce implants that are generally round, oval, square or rectangular, while the hand-cut implants could have serrated lines, sides and edges.

"Saucer-shaped" as used herein with respect to the tissue refers to a tissue that has a concave surface wherein the ends of the tissue do not extend beyond ½ of the distance between the vertex and the center of curvature. In various embodiments, the ends of the tissue do not extend beyond 1/20, 1/15, 1/10, 1/8, 1/5, 1/4, or 1/3 of the distance between the vertex and the center of curvature.

"Cup-shaped" as used herein with respect to the tissue refers to a tissue that has a concave surface wherein the ends of the tissue extend beyond ½ of the distance between the vertex and the center of curvature either along the curvature, or at a different angle after the ½ way point between the vertex and the curvature.

In various embodiments, the piece of tissue and/or second piece of tissue is sterilized. In various embodiments, the piece of tissue and/or second piece of tissue is free of pathogens, bacteria, viruses, funguses, and/or parasites.

In some embodiments, the piece of tissue and/or second piece of tissue is dimensioned to cover a surface of only one but not two bones in the joint. In certain embodiments, in the joint, only one bone's surface is covered by one piece of tissue. In certain embodiments, in the joint, two bones' two surfaces are covered by two separate pieces of issue. In certain embodiments, in the joint, two bones' two surfaces are not covered by the same piece of issue.

In some embodiments, the piece of tissue and/or second piece of tissue is dimensioned to cover an articular surface of only one but not two bones in the joint. In certain embodiments, in the joint, only one bone's articular surface is covered by one piece of tissue. In certain embodiments, in the joint, two bones' two articular surfaces are covered by two separate pieces of issue. In certain embodiments, in the joint, two bones' two articular surfaces are not covered by the same piece of issue.

In various embodiments, the piece of tissue and/or second piece of tissue is dimensioned to be inserted into the subject's joint.

In various embodiments, the piece of tissue and/or second piece of tissue is configured to be secured to a surface. In various embodiments, the surface is an articular surface.

In various embodiments, the piece of tissue and/or second piece of tissue is configured to be secured into cartilage when used for repairing osteochondral damages or defects.

In various embodiments, the implant further comprises a securement for securing the piece of tissue and/or second piece of tissue to their respective target surfaces or cartilage. In accordance with the present invention, the securement can be a suture, anchor, suture anchor, fibrin glue, screw, bolt, nail, pin, staple, fastener, ligament, or adhesive, or a combination thereof. In various embodiments, one or more securements may be used to securing the piece of tissue and/or second piece of tissue to the surface. As one non-limiting example, the piece of tissue and/or second piece of tissue may be sutured to the surface. As another non-limiting example, the piece of tissue and/or second piece of tissue may be glued to the surface. As still another non-limiting example, the piece of tissue and/or second piece of tissue may be sutured and glued to the surface.

Methods of Manufacturing

In various embodiments, the present invention provides a method of manufacturing an implant for implantation into a subject's joint. In various embodiments, the method comprises: obtaining a piece of tissue from a meniscus; and dimensioning the piece of tissue for covering a surface of a bone in a joint, whereby the dimensioned piece of tissue is the manufactured implant. In various embodiments, implant is configured for an articular surface. In various embodiments, the method comprises: obtaining a piece of tissue from a meniscus; and dimensioning the piece of tissue for covering a damage or defect in a joint, whereby the dimensioned piece of tissue is the manufactured implant.

In accordance with the present invention, the step of dimensioning can involve shaping the piece of tissue through cutting, trimming, and molding.

In some embodiments, dimensioning comprises shaping the piece of tissue to be round or generally round, oval or generally oval, square or generally square, or rectangular or generally rectangular. In some embodiments, dimensioning comprises shaping the piece of tissue to be flat, saucer-shaped or cup-shaped.

In various embodiments, dimensioning comprises shaping the piece of tissue to be about 0.2-4.0 cm$^2$. In various embodiments, dimensioning comprises shaping the piece of tissue to be about 0.2-0.3, 0.3-0.4, 0.4-0.5, 0.5-0.6, 0.6-0.7, 0.7-0.8, 0.8-0.9, 0.9-1, 1-2, 2-3, or 3-4 cm$^2$. In certain embodiments, dimensioning comprises shaping the piece of tissue to be about 0.2, 0.3, 0.2, 0.3, 0.4, 0.5, 0.6, 0.7, 0.8, 0.9, 1, 2, 3, or 4 cm$^2$. In particular embodiments, dimensioning comprises shaping the piece of tissue to be about 1.0, 1.1, 1.2, 1.3, 1.4, 1.5, 1.6, 1.7, 1.8, 1.9, 2.0, 2.1, 2.2, 2.3, 2.4, or 2.5 cm$^2$.

In various embodiments, dimensioning comprises shaping the piece of tissue to have a dimension (e.g., diameter, diagonal, width, or length) of about 0.2-4.0 cm. In various embodiments, dimensioning comprises shaping the piece of tissue to have a dimension (e.g., diameter, diagonal, width, or length) of about 0.2-0.3, 0.3-0.4, 0.4-0.5, 0.5-0.6, 0.6-0.7, 0.7-0.8, 0.8-0.9, 0.9-1, 1-2, 2-3, or 3-4 cm. In certain embodiments, dimensioning comprises shaping the piece of tissue to have a dimension (e.g., diameter, diagonal, width, or length) of about 0.3-0.5 or 0.5-3 cm. In certain embodiments, dimensioning comprises shaping the piece of tissue to have a dimension (e.g., diameter, diagonal, width, or length) of about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 cm. In some embodiments, dimensioning comprises shaping the piece of tissue to have dimensions of about 0.5 cm×0.5 cm, 0.5 cm×1 cm, 0.5 cm×2 cm, 0.5 cm×3 cm, 0.5 cm×4 cm, 1 cm×1 cm, 1 cm×2 cm, 1 cm×3 cm, 1 cm×4 cm, 2 cm×2 cm, 2 cm×3 cm, 2 cm×4 cm, 3 cm×3 cm, 3 cm×4 cm, or 4 cm×4 cm.

In various embodiments, dimensioning comprises shaping the piece of tissue to have a thickness of about 0.1-1.0 cm. In various embodiments, dimensioning comprises shaping the piece of tissue to have a thickness of about 0.1-0.2, 0.2-0.3, 0.3-0.4, 0.4-0.5, 0.5-0.6, 0.6-0.7, 0.7-0.8, 0.8-0.9, or 0.9-1 cm. In certain embodiments, dimensioning comprises shaping the piece of tissue to have a thickness of about 0.1-0.2 or 0.2-1 cm. In certain embodiments, dimensioning comprises shaping the piece of tissue to have a thickness of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm. The thickness can be uniform or non-uniform. For example, for a saucer-shaped tissue, the center of the tissue can be thicker than the edges.

In some embodiments, dimensioning comprises shaping the piece of tissue to be inserted into the subject's joint. In some embodiments, dimensioning comprises shaping the piece of tissue to be secured to the surface of the bone.

In various embodiments, the manufacturing method further comprises attaching a securement to the piece of tissue, wherein the securement is configured for securing the piece of tissue to the surface of the bone. In various embodiments, the surface is an articular surface. In various embodiments, the manufacturing method further comprises attaching a securement to the piece of tissue, wherein the securement is configured for securing the piece of tissue to cartilage. In some embodiments, the securement is a suture, anchor, suture anchor, screw, bolt, nail, pin, staple, fastener, ligament, or a combination thereof.

Methods of Treating

In various embodiments, the present invention provides a method of treating a subject's joint. The method may comprise: providing a piece of tissue harvested from a meniscus, wherein the piece of tissue is dimensioned to cover a surface of a bone in the joint; exposing the joint; preparing the surface; inserting the piece of tissue into the joint; securing the piece of tissue to the surface; and closing the joint. In various embodiments, the surface is an articular surface.

In various embodiments, the present invention provides a method of treating a subject's joint. The method may comprise: providing a piece of tissue harvested from a meniscus, wherein the piece of tissue is dimensioned to cover a surface of a bone in the joint; exposing the joint; preparing the surface; inserting the piece of tissue into the joint; securing the piece of tissue to the surface; providing a second piece of tissue harvested from a meniscus, wherein the second piece of tissue is dimensioned to cover a second surface of a second bone in the joint; preparing the second surface; inserting the second piece of tissue into the joint; securing the second piece of tissue to the second surface; and closing the joint.

In various embodiments, before closing the joint, a method as disclosed herein comprises suturing the piece of tissue and/or second piece of tissue to the surface. In various embodiments, before closing the joint, a method as disclosed herein comprises gluing he piece of tissue and/or second piece of tissue to the surface. In various embodiments, before closing the joint, the method further comprises coating the piece of tissue and/or second piece of tissue and the surface with a fibrin sealant glue.

While the situations of using one or two pieces of tissue are discussed, one of ordinary skill in the art would understand that as many pieces of tissue as necessary may be used to treat the subject's joint. For example, the present invention also contemplates using two, three, four, five, or more pieces of tissues to treat the subject's joint.

In various embodiments, the present invention provides a method of treating a subject's osteochondral damage or defect. The method may comprise: providing a piece of tissue harvested from a meniscus, wherein the piece of tissue is dimensioned to replace the damage or defect in the cartilage; removing the damage or defect in the cartilage and thereby creating a cavity in the cartilage; inserting the piece of tissue into the cavity; and securing the piece of tissue to the cartilage.

In various embodiments, a method as described herein may further comprise other treatments. Examples of these other treatments include but are not limited to medicine, surgery and physical therapy. As non-limiting examples, the subject may receive proximal carpectomy (PRC), scaphoid-ectomy with four-corner fusion (4CF), and hand therapy. In some embodiments, a method described herein is used as an adjunct therapy for these other treatments. In other embodiments, these other treatments are used as an adjunct therapy for a method disclosed herein. In some embodiments, a method described herein is performed before, during or after these other treatments. In various embodiments, a method disclosed herein and these other treatments are for the goal of treating the subject, regardless which is the primary or adjunct therapy or which is performed earlier or later.

In various embodiments, the subject is a human. In various embodiments, the subject is a mammalian subject. In various embodiments, the subject's joint is injured and/or arthritic.

In some embodiments, the joint is a small joint. Examples of a small joint include but are not limited to hand joints, finger joints, foot joints, and toe joints. In some embodiments, the joint is a medium joint. Examples of a medium joint include but are not limited to wrist joints and ankle joints. In some embodiments, the joint is a large joint. Examples of a large joint include but are not limited to elbow joints, shoulder joints, knee joints, and hip joints.

In some embodiments, the piece of tissue is dimensioned to cover a surface on the bone in a small, medium, or large joint. In some embodiments, the surface to be covered by the piece of tissue on the bone is an articular surface. In certain embodiments, the piece of tissue is dimensioned to cover the entire articular surface of a bone in a small, medium or large joint. In certain embodiments, the piece of tissue is dimensioned to cover merely part of the articular surface of a bone in a small, medium or large joint.

In various embodiments, the piece of tissue is secured (for example, sutured and/or glued) onto a cartilage as a patch repair of a damage or defect of the cartilage, for example osteochondral damages or defects. In some embodiments, the damage or defect is in a joint.

As one non-limiting example, in a situation where the cartilage in a joint is damaged, the damaged portion of the cartilage is removed, a piece of meniscus of the appropriate size is provided, and the piece of meniscus is sutured and/or glued into the cartilage.

In some embodiments, the subject's joint is a metacarpophalangeal joint. In various embodiments, the subject's joint is an interphalangeal joint, distal interphalangeal joint, or proximal interphalangeal joint.

In some embodiments, the joint is a joint on the arm or hand. In some embodiments, the subject's joint is a joint of hand. In various embodiments, the joint is the shoulder joint, elbow joint, wrist joint, hand joint, or finger joint.

In some embodiments, the subject's joint is an intercarpal, midcarpal, carpometacarpal, or intermetacarpal joint. In some embodiments, the subject's joint is a proximal radioulnar or distal radioulnar joint. In some embodiments, the subject's joint is a radiocarpal joint. In some embodiments, the subject's joint is a humeroradial or humeroulnar joint. In some embodiments, the subject's joint is a sternoclavicular, acromioclavicular, or glenohumeral joint.

In various embodiments, the bone to be covered by the piece of tissue and/or the second piece of tissue is clavicle, scapula, humerus, ulna, radius, carpal, scaphoid, lunate, triquetral, pisiform, trapezium, trapezoid, capitate, and hamate, metacarpal, proximal phalange, intermediate phalange, distal phalange, or phalange. In some embodiments, the surface to be covered by the piece of tissue and/or the second piece of tissue is in a joint. In various embodiments, the bone's surface to be covered by the piece of tissue and/or the second piece of tissue is an articular surface.

In some embodiments, the joint is a joint on the leg or foot. In some embodiments, the subject's joint is a joint of foot. In various embodiments, the joint is the hip joint, knee joint, ankle joint, foot joint or toe joint.

In some embodiments, the subject's joint is a metatarsophalangeal joint. In some embodiments, the subject's joint is an intermetatarsal or metatarsal joint. In some embodiments, the subject's joint is a tarsometatarsa or Lisfranc joint. In some embodiments, the subject's joint is a cuneonavicular, cuboideonavicular, or intercuneiform joint. In some embodiments, the subject's joint is a distal intertarsal joint. In some embodiments, the subject's joint is a talocalcaneonavicular or calcaneocuboid joint. In some embodiments, the subject's joint is a transverse tarsal or midtarsal joint. In some embodiments, the subject's joint is a talocrural, subtalar, or talocalcaneal joint. In some embodiments, the subject's joint is a superior tibiofibular or inferior tibiofibular joint. In some embodiments, the subject's joint is a tibiofemoral or patellofemoral joint.

In various embodiments, the bone to be covered by the piece of tissue and/or the second piece of tissue is acetabulum of the pelvis, femur, tibia, fibula, patella, tarsal, talus, calcaneus, cuboid, navicular, cuneiform, medial cuneiform intermediate cuneiform, lateral cuneiform, metatarsal, proximal phalange, intermediate phalange, distal phalange, or phalange. In some embodiments, the surface to be covered by the piece of tissue and/or the second piece of tissue is in a joint. In various embodiments, the bone's surface to be covered by the piece of tissue and/or the second piece of tissue is an articular surface.

In various embodiments, the piece of tissue and/or second piece of tissue is an allograft, xenograft, isograft, or autograft. In some embodiments, the meniscus is harvested from a human. In other embodiments, the meniscus is harvested from another mammalian. Examples of mammalians include but are not limited to pig, cattle, bull, cow, sheep, goat, horse, donkey, mule, hinny, ape, monkey, ape, or chimpanzee. In various embodiments, the meniscus is harvested from a cadaver. In various embodiments, the meniscus is harvested from a knee, acromioclavicular, sternoclavicular, temporomandibular joint or radio-carpal joint. In particular embodiments, the meniscus is harvested from a knee. In other particular embodiments, the meniscus is human cadaver knee meniscus.

In some embodiments, the piece of tissue is dimensioned to cover the entire articular surface of a bone. In other embodiments, the piece of tissue is dimensioned to cover merely part of the articular surface of a bone. In some embodiments, the piece of tissue, after being secured to a bone, resurfaces the entire articular surface of the bone. In other embodiments, the piece of tissue, after being secured to a bone, resurfaces merely part of the articular surface of the bone.

In various embodiments of the present invention, the meniscus is not used as a spacer. In various embodiments of the present invention, the meniscus is not similar to the spacer used for treating hallux rigidus of the first metatarsophalangeal (MTP) joint, for example, those described in DelaCruz et al. (First metatarsophalangeal joint interpositional arthroplasty using a meniscus allograft for the treatment of advanced hallux rigidus: surgical technique and short-term results, Foot Ankle Spec. 2011 June; 4(3):157-64. Epub 2011 Apr. 13.) In various embodiments of the present invention, the meniscus is not shaped like a tortellini. In various embodiments of the present invention, the meniscus is not similar to the spacer used for the thumb, for example, those constructed from human acellular dermal matrix (HADM) or FlexHD (see e.g., Yao et al., Preserving the Posttrapeziectomy Space with a Human Acellular Dermal Matrix Spacer: A Pilot Case Series of Patients with Thumb Carpometacarpal Joint Arthritis, Plast Reconstr Surg Glob Open. 2013 October; 1(7): e65).

Instead of using meniscus as a spacer, embodiments of the present invention recontour a meniscus according to a joint so that the meniscus takes the shape and function of the original joint. In various embodiments, the joint is resurfaced with the meniscus, which can be more durable than cartilage. Other embodiments of the present invention use pieces of meniscus to replace damages or defects in cartilage.

In some embodiments, the bone in the joint that is to be covered by the piece of tissue is a carpal bone. In some embodiments, the bone in the joint that is to be covered by the piece of tissue is a metacarpal bone. In some embodiments, the bone in the joint that is to be covered by the piece of tissue is a phalangeal bone.

As a non-limiting example, a radiocarpal joint may be reconstructed with a procedure as shown in FIGS. 6A-6L: exposing the radiocarpal joint; debriding the articular surfaces of capitate 605 and lunate 608; providing a meniscus 606 that is harvested from a cadaver, outlining it to a dimension for covering the articular surfaces, and cutting a piece of tissue out of it according to the outline; inserting the piece of tissue into the radiocarpal joint; suturing the piece of tissue to the articular surfaces; coating the sutured area with fibrin sealant glue 613; and closing the joint while preserving joint space. While in this non-limiting example, the meniscus is not cut prior to the surgery to a dimension suitable for covering the articular surfaces, the present invention certainly contemplates providing menisci that are already cut prior to surgeries to various dimensions suitable for covering various surfaces of the bone, including articular surfaces of the bone; in other words, the present invention provides off-the-shelf meniscus implants of various dimensions for direct use by a surgeon without further preparation. Labels used in FIGS. 6A-6L are: 601 EPL TENDON; 602 PENROSE DRAIN; 603 ECRL AND ECRB TENDON; 604 SKIN; 605 CAPITATE; 606 CADAVERIC MENISCUS; 607 EDC TENDON; 608 LUNATE; 609 RADIUS; 610 EDC; 611 PART OF LUNATE; 612 SUTURES; 613 FIBRIN SEALANT GLUE; and 614 RADIOCARPAL JOINT.

As another non-limiting example, a metacarpophalangeal joint may be reconstructed with a procedure as shown in FIGS. 7A-7D: exposing the metacarpophalangeal joint; debriding the articular surfaces of phalange 701 and metacarpal 702; providing two menisci 703 that are harvested from a cadaver, outlining them to dimensions for covering the two articular surfaces, and cutting two pieces of tissue out of them according to their respective outlines; inserting the two pieces of tissue into the metacarpophalangeal joint; suturing the two piece of tissue to the articular surfaces; optionally, coating the sutured area with fibrin sealant glue; and closing the joint while preserving joint space. While in this non-limiting example, the meniscus is not cut prior to the surgery to a dimension suitable for covering the articular surfaces, the present invention certainly contemplates providing menisci that are already cut prior to surgeries to various dimensions suitable for covering various surfaces of the bone, including articular surfaces of the bone; in other words, the present invention provides off-the-shelf meniscus implants of various dimensions for direct use by a surgeon without further preparation. Labels used in FIGS. 7A-7D are: 701 PHALANGE; 702 METACARPAL; 703 CADAVERIC MENISCUS; 704 SKIN; and 705 SUTURES.

In some embodiments, one bone in the joint is covered, and the other bone in the joint is not covered. In other embodiments, one bone in the joint is covered with a piece of tissue, and the other bone in the joint is covered by a second piece of tissue. In some embodiments, the second bone in the joint that is to be covered by the second piece of tissue is a carpal bone. In some embodiments, the second bone in the joint that is to be covered by the second piece of tissue is a metacarpal bone. In some embodiments, the second bone in the joint that is to be covered by the second piece of tissue is a phalangeal bone.

The dimensions, thickness, shapes and sources for the implants used in these treatment methods can be those as discussed above.

Kits

In various embodiments, the present invention provides a kit treating a subject's joint. In some embodiments, the kit may comprise: one or more pieces of tissue (e.g., 1, 2, 3, 4, 5) harvested from a meniscus, wherein the one or more pieces of tissue are dimensioned to cover one or more surfaces of one or more bones in the joint; and instructions for using the one or more pieces of tissue to treat the subject's joint. In other embodiments, the kit may comprise: one or more pieces of tissue (e.g., 1, 2, 3, 4, 5) harvested from a meniscus, wherein the one or more pieces of tissue are dimensioned replace damaged cartilage; and instructions for using the one or more pieces of tissue to replace damaged cartilage. In other embodiments, the kit may consist of or consist essentially of: one or more pieces of tissue harvested from a meniscus, wherein the one or more pieces of tissue are dimensioned to cover one or more surfaces of one or more bones in the joint; and instructions for using the one or more pieces of tissue to treat the subject's joint. In other embodiments, the kit may consist or consist essentially of: one or more pieces of tissue (e.g., 1, 2, 3, 4, 5) harvested from a meniscus, wherein the one or more pieces of tissue are dimensioned replace damaged cartilage; and instructions for using the one or more pieces of tissue to replace damaged cartilage.

In various embodiments, the kit may further comprise one or more securements for securing the one or more pieces of tissue to the one or more surfaces. In accordance with the present invention, the securement can be a suture, anchor, suture anchor, fibrin glue, screw, bolt, nail, pin, staple, fastener, ligament, or adhesive, or a combination thereof.

The kit is an assemblage of materials or components. The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, scalpels, scissors, forceps, clamps, bur, syringes, applicators (for example, applicators of glue (e.g., fibrin glue)), suturing needles, sutures, anchors, suture anchors, bandaging materials, analgesic, spray bottles or cans, diluents, buffers, pharmaceutically acceptable carriers, catheters, pipetting or measuring tools, templates for sizing a joint, and templates for cutting a meniscus into implants of desirable sizes and shapes, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive implants and the like. The packaging material is constructed by well-known methods, preferably to provide a sterile, contaminant-free environment. The packaging materials employed in the kit can be those customarily utilized in therapies and surgeries. As used herein, the term "package" refers to a suitable solid matrix or material such as glass, plastic, paper, foil, and the like, capable of holding the individual kit components. Thus, for example, a package can be a glass container used to contain suitable quantities of implants as described herein. The packaging material generally has an external label which indicates the contents and/or purpose of the kit and/or its components.

Many variations and alternative elements have been disclosed in embodiments of the present invention. Still further variations and alternate elements will be apparent to one of skill in the art. Among these variations, without limitation, are the selection of constituent modules for the inventive components, and the diseases and other clinical conditions that may be diagnosed, prognosed or treated therewith. Various embodiments of the invention can specifically include or exclude any of these variations or elements.

In some embodiments, the numbers expressing quantities, sizes, dimensions (e.g., diameter, diagonal, width, or length), thickness, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention.

One skilled in the art may develop equivalent means or reactants without the exercise of inventive capacity and without departing from the scope of the invention.

Example 1

A Novel Use of Meniscus for Small Joint Reconstruction of the Hand

Small joint arthroplasty of the hand has mixed outcomes and no ideal implant has been developed. Various materials have been used in the past with mixed results. One of the classic reconstruction modalities is the silicone implant however one of the major drawbacks is that up to 40% of implants will break over long term follow up. Pyrolytic carbon is another synthetic substance which has been used with continued mixed results. This invention provides a novel approach for small joint reconstruction: using cadaveric meniscus for joint reconstruction. Meniscus is advantageous as it is amenable to a synovial environment, can be revascularized, has a low metabolic demand, and is malleable.

The inventor reconstructed three metacarpophalangeal (MCP) and one proximal interphalangeal joint (PIP) in four patients using cadaveric meniscus. Patient demographic, pre- and post-operative pain and range of motion data was examined as well as operative technique.

Figure 2:
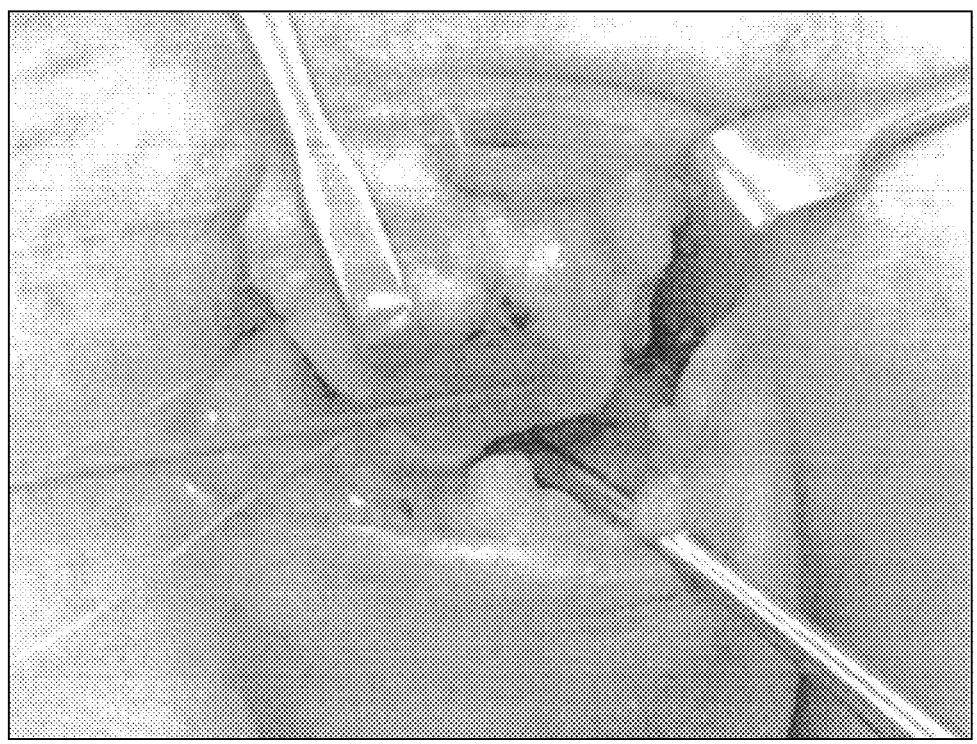
FIG. 2 depicts, in accordance with various embodiments of the invention, the small joint reconstruction on Patient 1.
Figure 3:
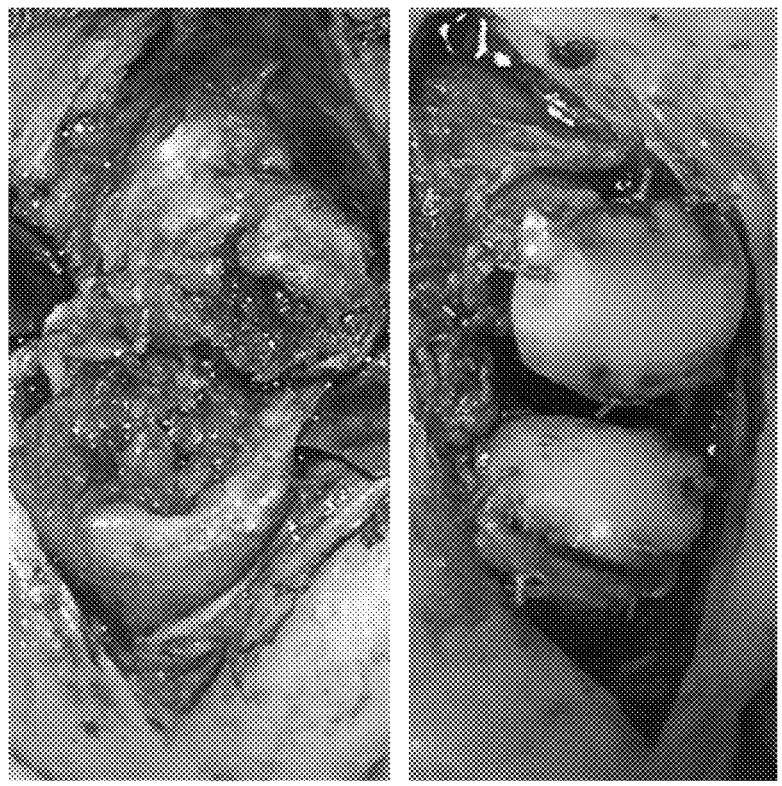
FIG. 3 depicts, in accordance with various embodiments of the invention, the small joint reconstruction on Patient 3. Articular surfaces of the MCP join debrided on left and with inset meniscus on right.

Three patients had monoarticular arthritis of the metacarpopharyngeal joint and had failed medical treatment. The MCP joint was burred and meniscus was used to fill the contour defect that remained on both proximal and distal aspects and sutured with 4-0 mersiline (FIG. 3). Patient 1 is a 58 year old right hand male who works as an artist presenting with monoarticular arthritis of the right 3rd MCP joint who had failed medical treatment. Patient had the MCP joint burred (FIG. 1) and meniscus was used to fill the contour defect that remained and sutured with 4-0 mersiline (FIG. 2). The same method was used for Patient 2, a 51 year old orthodontist, with previous trauma to the 5th MCP joint. Patient 3, a 38 year old actress, also required reconstruction of the 2nd MCP joint. However, her injury was due to previous septic shock with end organ damage. Both articular surfaces were debrided and inset with meniscus (FIG. 3).

Figure 4:
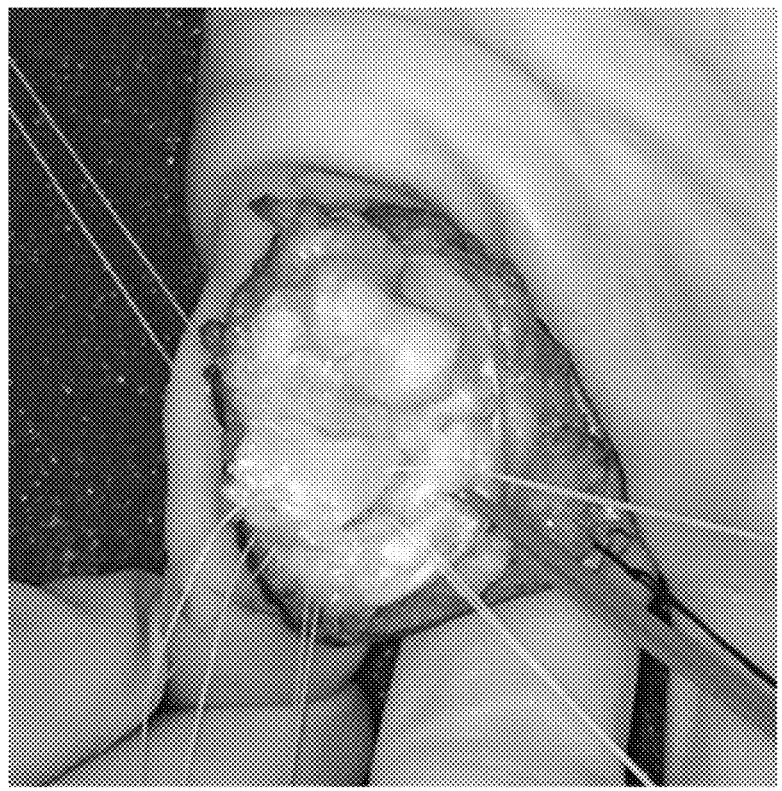
FIG. 4 depicts, in accordance with various embodiments of the invention, the small joint reconstruction on Patient 4. Meniscus was inserted in the proximal interphalangeal (PIP) joint.
Figure 5A:
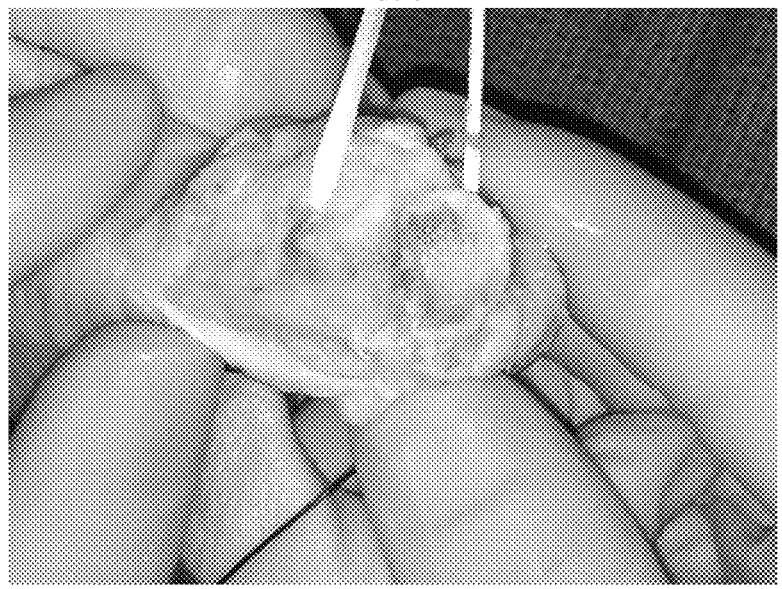
FIGS. 5A-5B depict, in accordance with various embodiments of the invention, finger salvage of the proximal interphalangeal (PIP) joint using cadaver meniscus.
Figure 5B:
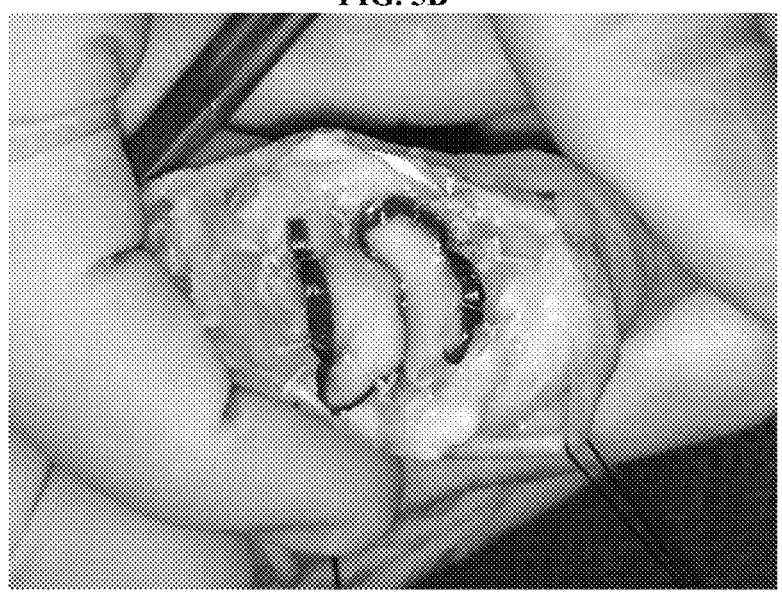

One patient suffered arthritis to the PIP joint of the 5th digit with limited range of flexion. Patient 4 is a 52 year old female who works as a lawyer with previous history of trauma to the left PIP joint of the 5th digit. Patient had been initially operated on however had a continued deformity of the PIP joint with limited range of flexion to only 60 degrees and significant arthritis. The patient was found to have a large volar lip of the middle phalanx that was removed and meniscus was then placed into the joint in a similar fashion as in the metacarpophalangeal joint (FIG. 4). Another example of PIP is shown in FIGS. 5A-5B.

All patients underwent early hand therapy and had improvement of pain and range of motion of the affected joint. There were no complications, and no revisions were necessary.

Multiple modalities have been used to reconstruct the small joints of the hand with mixed results. This invention demonstrates that meniscus is an option for reconstruction to help with motion and pain with the added benefit of malleability, potential for revascularization and resilience. This technology can also be used to reconstruct arthritic joints in the hand as a result of traumatic or aging process.

Example 2

Wrist Salvage of the Radiocarpal Joint Using Cadaver Meniscus

In the setting of wrist salvage, proximal row carpectomy (PRC) and scaphoidectomy with four-corner fusion (4CF) are effective motion-preserving and pain-relieving therapies. Effective treatment necessitates that the capitolunate joint remains free of osteochondral defects to achieve pain-free motion and healing. In patients with severe arthritis in the capitolunate joint, we propose a novel adjunct for PRC wrist joint salvage using cadaveric meniscus for joint resurfacing. It is an off-the-shelf alternative that is not only malleable but also addresses focal osteochondral effects and restores intra-articular contact stress distributions toward normal levels.

The inventors reconstructed three radiocapitate joints with osteochondral defects using cadaveric meniscus to facilitate PRC of the wrist and preserve pain-free motion. Patient demographic, pre and post-operative pain and range of motion data was examined as well as operative complications.

Figure 6A:
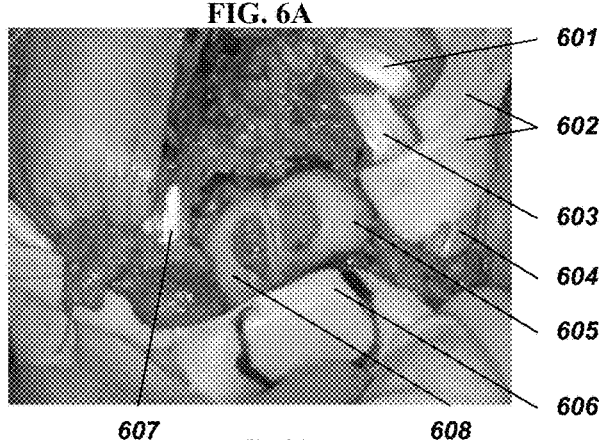
FIGS. 6A-6L depict, in accordance with various embodiments of the invention, wrist salvage of the radiocarpal joint using cadaver meniscus.
Figure 6B:
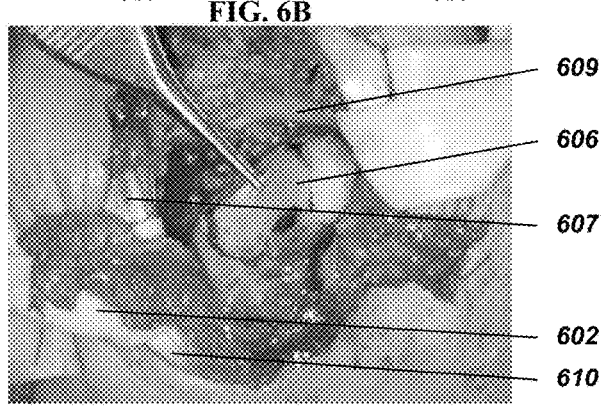
Figure 6C:
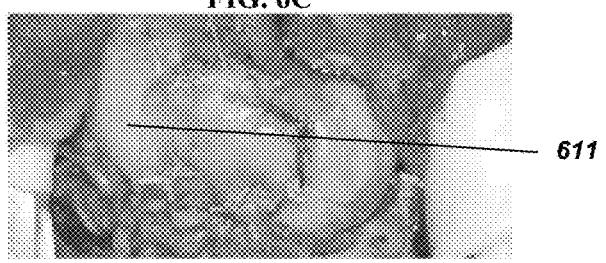
Figure 6D:
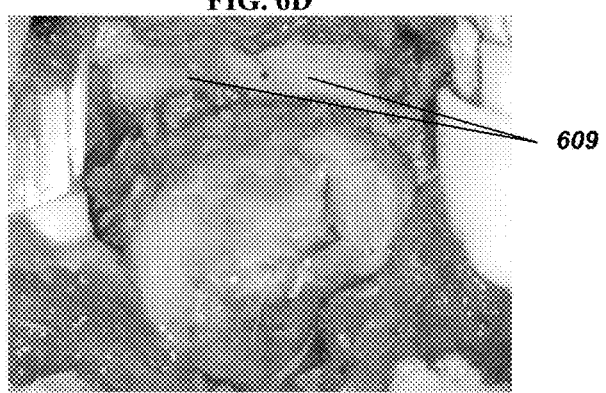
Figure 6E:
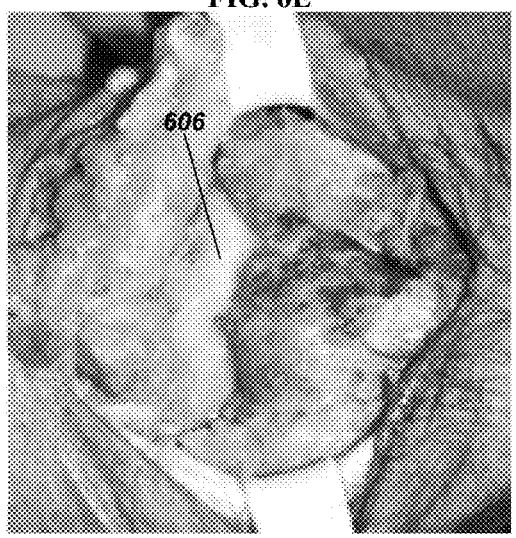
Figure 6F:
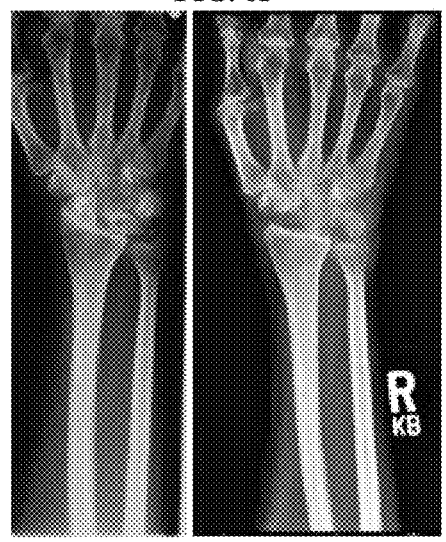
Figure 6G:
Figure 6H:
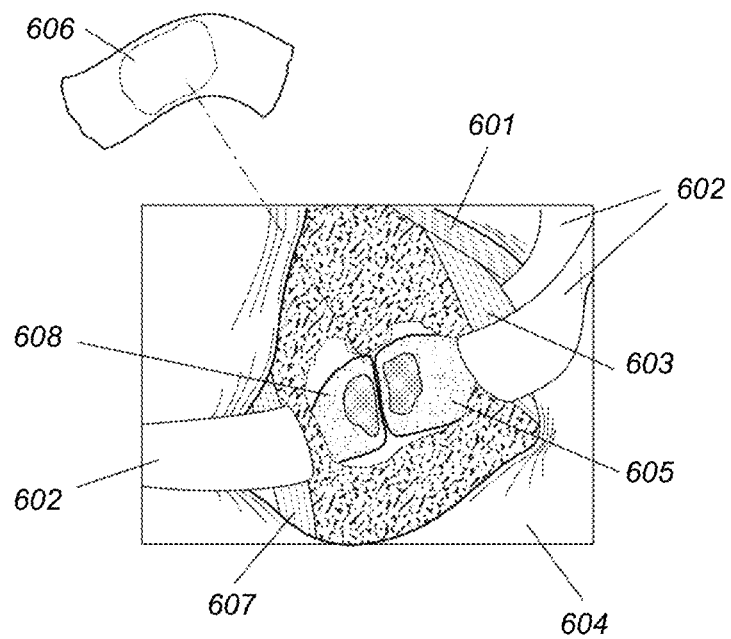
Figure 6I:
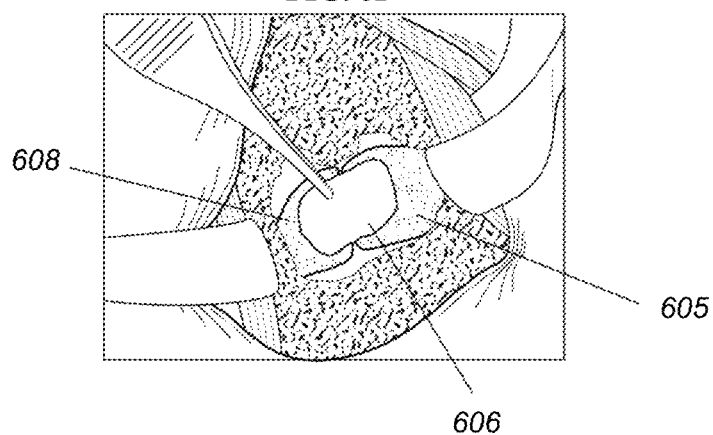
Figure 6J:
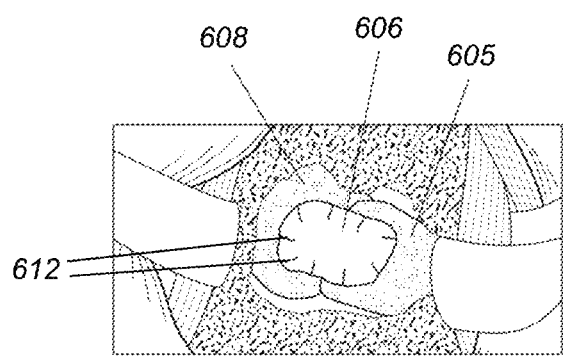
Figure 6K:
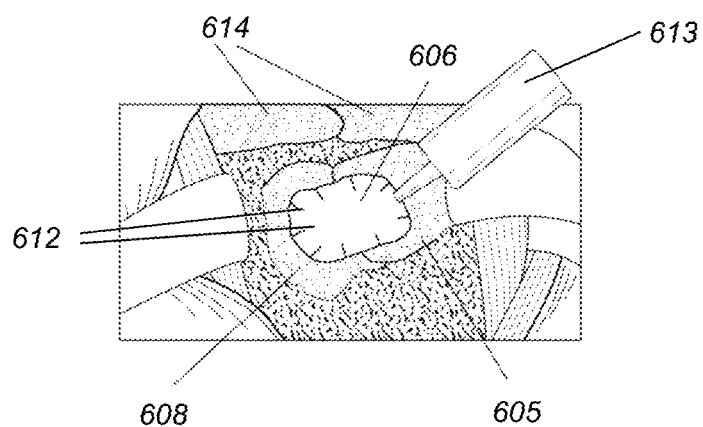
Figure 6L:
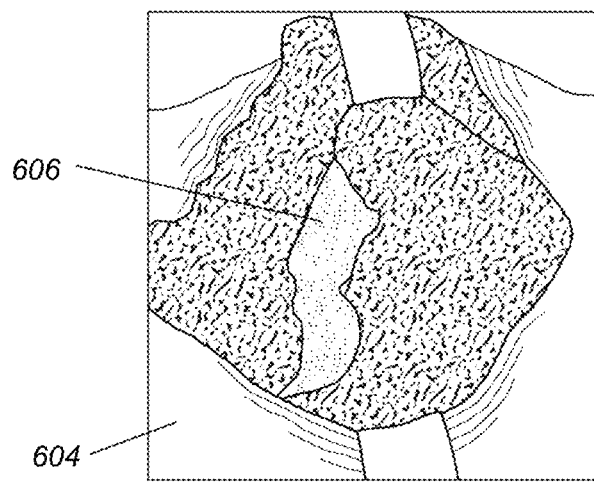
Figure 7A:
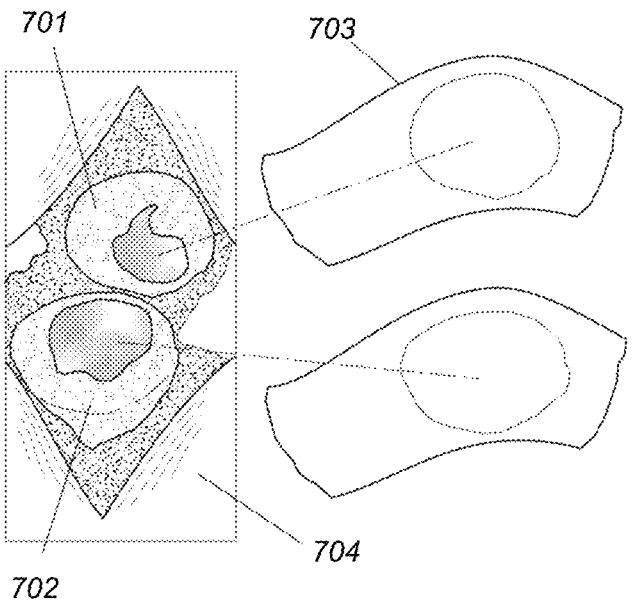
FIGS. 7A-7D depict, in accordance with various embodiments of the invention, a rendering of the procedure of reconstructing a metacarpophalangeal joint with cadaveric meniscus. The phalange 701 and metacarpal 702 articular surfaces are debrided, and two menisci 703 are outlined to dimensions for covering the two articular surfaces and then cut accordingly (7A); osteochondral defects are inset with the two menisci (7B); the two menisci are sutured to the two articular surfaces (7C); the two menisci and the two articular surfaces may optionally be coated with fibrin sealant glue; and the joint is closed while joint space is preserved intraoperatively (7D).
Figure 7B:
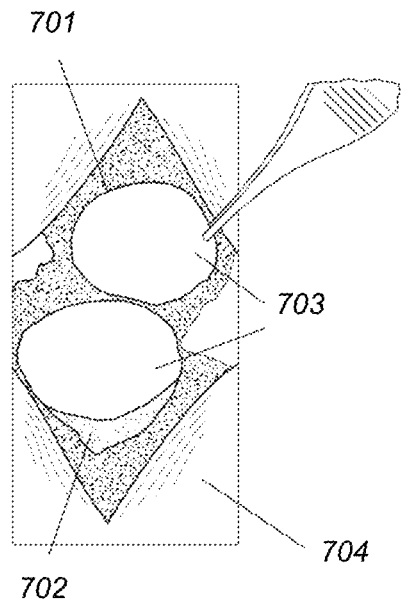
Figure 7C:
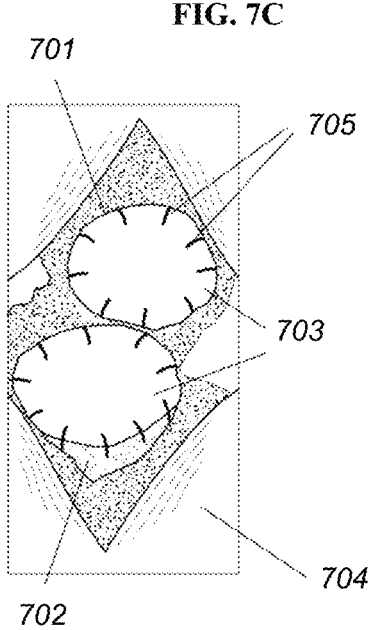
Figure 7D:
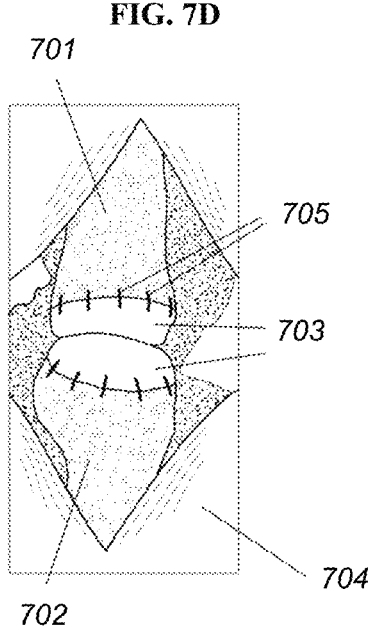

Three patients aged 50 to 73 years old underwent PRC treatment for severe, painful and motion limiting wrist arthritis secondary to traumatic scaphoid non-union (n=1) and scaphoid-lunate advanced collapse (n=2). Each patient underwent successful PRC of the wrist (2 right, 1 left) and debridement of the radiolunate facet and proximal capitate articular surfaces (FIGS. 6A and 6H). Osteochondral defects were inset with meniscus 3 cm×1 cm (FIGS. 6B and 6I), sutured (FIGS. 6C and 6J), and coated with fibrin sealant glue (FIGS. 6D and 6K). Intraoperatively, joint space was preserved (FIGS. 6E and 6L). All patients underwent early hand therapy, and had significant reduction in pain (average pain scale reduction from severity of 10 to 3) as well as improvement in their affected wrist range of motion (average 15 degrees for wrist extension and 30 degrees of wrist flexion). There were no complications and no revisions were necessary. Postoperative films identify preservation of radiocapitate joint space in patients with SNAC and SLAC wrists (FIGS. 6F and 6G, respectively) after several months during follow-up.

Multiple modalities have been used to salvage the joints of the wrist, but patients that are not candidates for PRC salvage due to radiocapitate arthrosis often resort to total wrist arthrodesis to address chronic pain. We demonstrate that meniscus is a viable adjunct option to PRC salvage and can be used to reconstruct wrist joints to preserve pain-free motion. Furthermore, cadaveric meniscus advantageously thrives in a synovial environment, maintains a low metabolic demand, biointegrates through revascularization and cellular repopulation, and is surgically malleable. As such, we prove that cadaveric meniscus is a good alternative for wrist salvage.

Example 3

Tissue Engineering Using Cadaveric Meniscus for Arthroplasty of the Hand: Long Term Outcomes

The use of small joint arthroplasty implants has been tinctured with mixed short and long term outcomes over the past 50 years. There have been several synthetic, non-biological materials developed to help recreate joint function. One classic reconstruction method utilizes silicone implants which initially provide excellent mechanical properties, however over the long term, up to 40% of these breaks or loses function. The ideal reconstruction would provide the biomechanical properties of the joint, but would also be biointegrated or at least biologically inert. One reconstructive approach involves the use of naturally derived human meniscus. As a biomaterial, meniscus is amenable to a synovial environment, it can be revascularized and biointegrated, it has a relatively low metabolic demand, and it is incredibly malleable. Described herein, cadaveric meniscuses are used for small joint reconstruction of the hand in 12 patients.

We reconstructed the small joints of the hand in twelve patients using cadaveric meniscus. Patient demographic, pre and post-operative pain and range of motion data were examined as well as operative technique. We review outcomes in the patients who have had reconstructions using these techniques and provide an update on the long term outcomes of the use of these biological reconstructions.

There were twelve total patients in the retrospective chart review. Patients presented with a variety of indications for surgery, including osteoarthritis, as well as traumatic arthritis with limitations in the range of motion as well as pain in the affected joints. All patients underwent early hand therapy and had improvement of pain and range of motion of the affected joint. There were no complications, and no revisions were necessary. The long term follow up of these patients involved examination in the office, comparison of range of motion and grip strength.

Though several methods are acceptable for small joint reconstruction of the hand, we are now approaching a time where off the shelf biological materials, as well as tissue engineered constructs are now coming into the clinical arena. Naturally derived biological materials can provide a viable option for reconstruction to help with motion and pain with the added benefit of malleability, potential for revascularization and long term durability.

Example 4

Long Term Successful Wrist and Finger Joint Salvage Using Cadaveric Meniscus for Osteochondral Defects in the Radiocarpal, Metacarpal, and Proximal Interphalangeal Joints

Osteochondral defects of the radiocarpal, metacarpophalangeal, and proximal-interphalangeal joints often necessitate joint arthrodesis or mechanical arthroplasty, which has a limited lifespan. In severely arthritic wrist and finger joints, we provide a novel adjunct for joint salvage using cadaveric meniscus for joint resurfacing as an off-the-shelf alternative to address focal osteochondral defects and restore normal intra-articular contact stress.

Five radiocapitate, five metacarpophalangeal, and two proximal-interphalangeal joints with osteochondral defects received cadaveric meniscus to facilitate arthroplasty. Patient demographic, peri-operative pain, range of motion, and complications were examined.

Patients aged 17 to 73 years old underwent joint reconstruction for scaphoid non-union (n=1), scaphoid-lunate advanced collapse (n=4), or osteoarthritis of MCP (n=5) or PIP (n=2) joints. Successful arthroplasty with joint space preservation occurred in all joints. Patients underwent post-operative hand therapy at 3 weeks and had significant reduction in pain scale score (average 10 to 1.4) and improved range of motion: average degrees flexion 15 (wrist), 46 (MCP), 40 (PIP), and extension 30 (wrist). No complications resulted; only a revision tenolysis and capsulotomy were required for PIP and MCP arthroplasties.

Postop films reveal preservation of arthroplasty joint space after an average 12.7 months follow-up.

We demonstrate that meniscus is a viable joint salvage adjunct to preserve pain-free motion and avoid total joint arthrodesis. Cadaveric meniscus advantageously maintains a low metabolic demand, biointegrates, and is surgically malleable.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of reconstructing a subject's joint, comprising:
   providing a piece of tissue harvested from a meniscus,
      wherein the piece of tissue harvested from the meniscus is recontoured according to the joint and dimensioned to cover an entire surface of a bone in the joint and takes the shape and function of the original joint,
      wherein the piece of tissue harvested from the meniscus is not shaped like tortellini, and
      wherein the piece of tissue harvested from the meniscus is shaped to be round or generally round, oval or generally oval, square or generally square, or rectangular or generally rectangular;
   exposing the joint;
   preparing the surface of the bone comprising decorticating the bone to expose medullary cortex of the bone and using a reamer to create a cup configuration and/or a cup joint configuration;

inserting the piece of tissue into the joint to cover the prepared surface of the bone to resurface the joint;

securing the piece of tissue to the surface; and closing the joint.

2. The method of claim 1, before closing the joint, further comprising:

providing a second piece of tissue harvested from a meniscus, wherein the second piece of tissue is dimensioned to cover a second surface of a second bone in the joint;

preparing the second surface;

inserting the second piece of tissue into the joint; and securing the second piece of tissue to the second surface.

3. The method of claim 1, wherein the joint is injured and/or arthritic.

4. The method of claim 1, wherein the surface is an articular surface.

5. The method of claim 1, wherein the meniscus is from a cadaver.

6. The method of claim 1, wherein the subject's joint is a finger joint.

7. The method of claim 1, wherein the subject's joint is a toe joint.

8. The method of claim 1, wherein the piece of tissue is shaped to be saucer-shaped or cup-shaped.

9. The method of claim 1, wherein the piece of tissue is dimensioned to be about 0.2-4.0 $cm^2$.

10. The method of claim 1, wherein the piece of tissue has a length or width of about 0.2-4.0 cm.

11. The method of claim 1, wherein the piece of tissue has a thickness of about 0.1-1.0 cm.

12. The method of claim 1, further comprising using a securement for securing the piece of tissue to the surface.

13. The method of claim 12, wherein the securement is a suture, adhesive, or a combination thereof.

* * * * *